(12) United States Patent
O'Rourke et al.

(10) Patent No.: US 8,435,184 B2
(45) Date of Patent: May 7, 2013

(54) CHARACTERISATION OF AGEING EFFECT AND CARDIOVASCULAR RISK

(75) Inventors: Michael O'Rourke, Hunters Hill (AU); Dean Winter, Helotes, TX (US)

(73) Assignee: Aortic Wrap Pty Ltd., Darlinghurst, New South Wales (AU)

( * ) Notice: Subject to any disclaimer, the term of this patent is extended or adjusted under 35 U.S.C. 154(b) by 851 days.

(21) Appl. No.: 12/525,014

(22) PCT Filed: Jan. 31, 2008

(86) PCT No.: PCT/AU2008/000149
§ 371 (c)(1),
(2), (4) Date: Oct. 9, 2009

(87) PCT Pub. No.: WO2008/092215
PCT Pub. Date: Aug. 7, 2008

(65) Prior Publication Data
US 2010/0121203 A1 May 13, 2010

(30) Foreign Application Priority Data
Jan. 31, 2007 (AU) ................................ 2007900435

(51) Int. Cl.
*A61B 5/02* (2006.01)
(52) U.S. Cl.
USPC ............................ 600/500; 600/481; 600/502
(58) Field of Classification Search ........... 600/481–528
See application file for complete search history.

(56) References Cited

U.S. PATENT DOCUMENTS
2003/0135124 A1* 7/2003 Russell ........................ 600/500

FOREIGN PATENT DOCUMENTS
EP  0664102 A2  7/1997
RU  2296501 C2  4/2007

OTHER PUBLICATIONS

International Preliminary Report on Patentability for International Application No. PCT/AU2008/000149, International Bureau of WIPO, Geneva, Switzerland, mailed on Aug. 13, 2009.
Sherebrin, et al., "Frequency Analysis of the Peripheral Pulse Wave Detected in the Finger with a Photoplethysmograph", *IEEE Trans. Biomed.Eng 37*:313-317 (1990).

* cited by examiner

*Primary Examiner* — Michael Kahelin
*Assistant Examiner* — Karen Toth
(74) *Attorney, Agent, or Firm* — Sterne, Kessler, Goldstein & Fox PLLC

(57) ABSTRACT

A method of determining ageing effect and cardiovascular risk in a human patient comprising: - (i) measuring the arterial pulse waveform of the patient when the heart is beating regularly, (ii) extracting the frequency dependent components of the pulse waveform, (iii) determining the ratio of the amplitude based value of the first harmonic ($H_1$) to the amplitude based value of a selected higher harmonic to provide an index of arterial ageing, and (iv) Comparing the index to normative values of index of arterial ageing to determine ageing effect and cardiovascular risk. Other methods of calculating the index based on harmonic amplitudes and the phase angle are also disclosed and claimed.

18 Claims, 16 Drawing Sheets

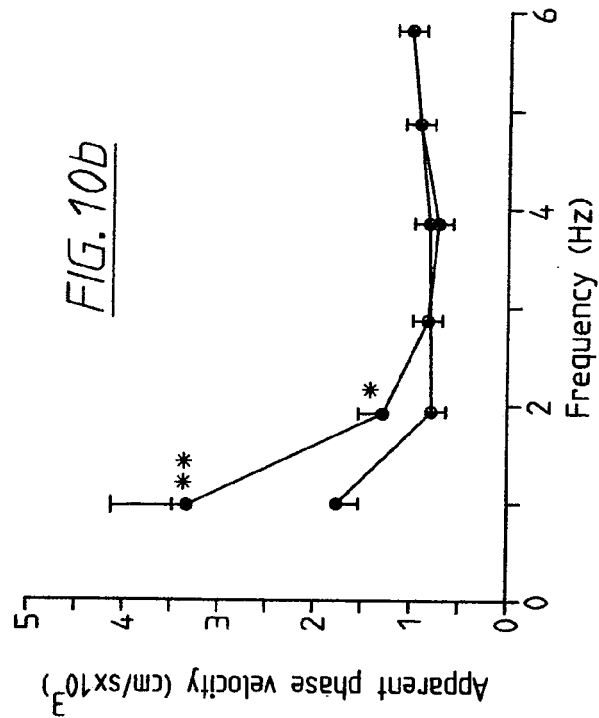
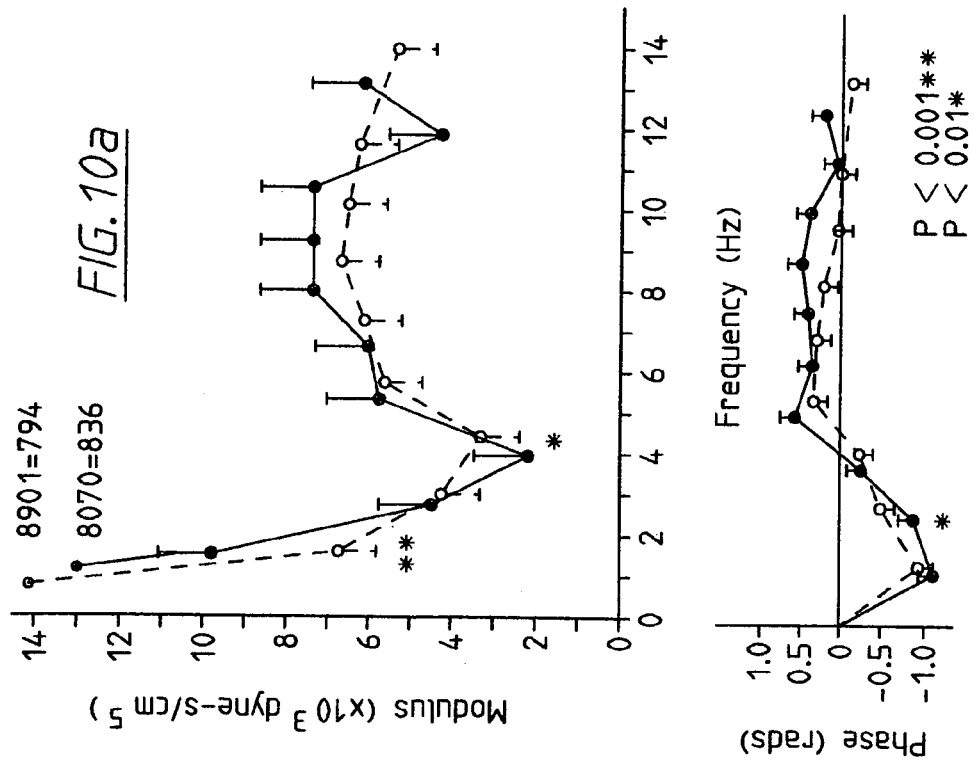
FIG.10a
FIG.10b

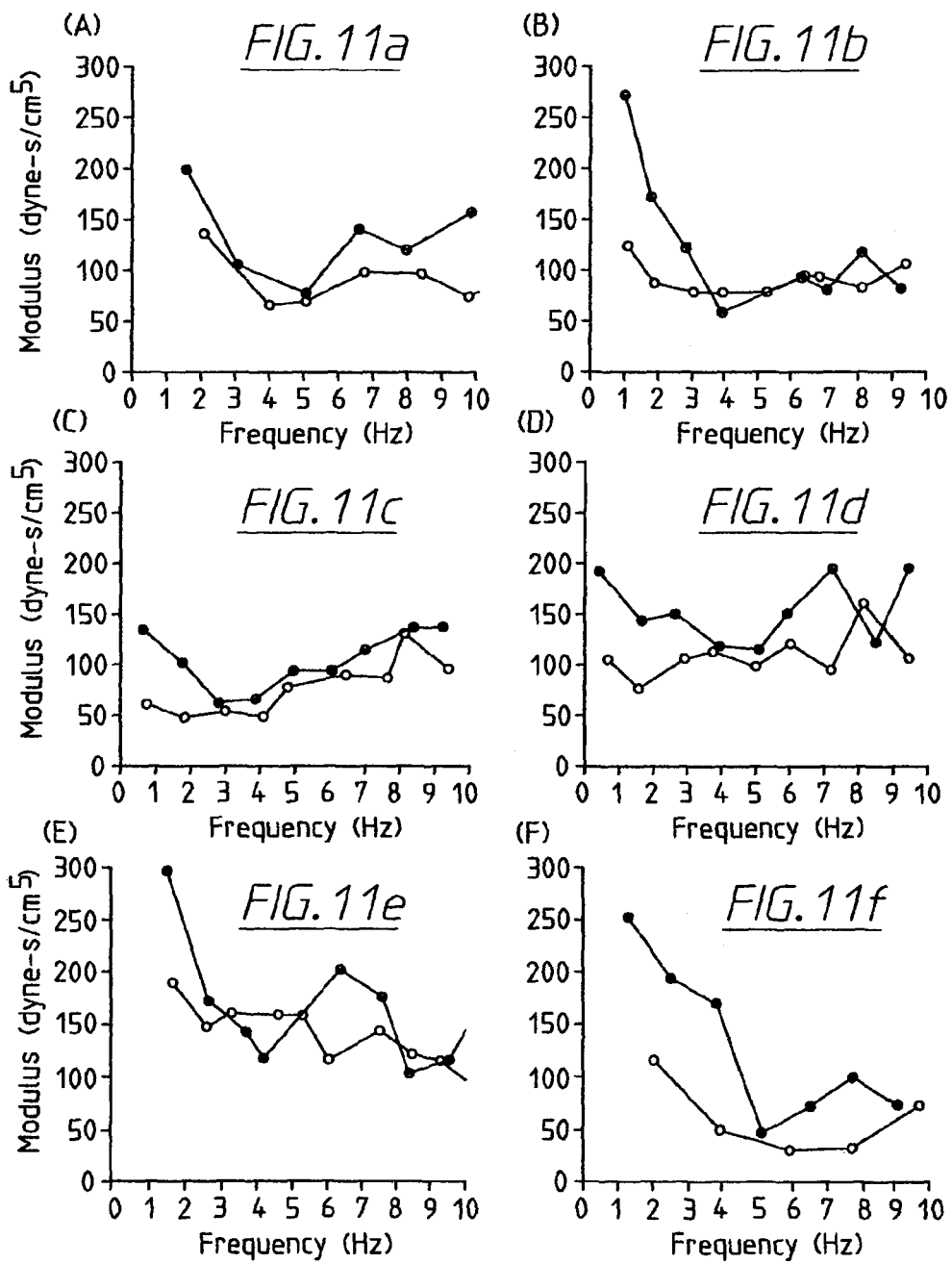

CHARACTERISATION OF AGEING EFFECT AND CARDIOVASCULAR RISK

TECHNICAL FIELD

This invention relates to the characterisation of ageing effect and cardiovascular risk in humans and, more particularly, to the determination of ageing effect and cardiovascular risk in adult patients from the arterial pulse waveform in the upper body, including neck, arms and fingers.

BACKGROUND ART

With stiffening of proximal elastic arteries with age, the ability of the arterial system to cushion flow pulsations is progressively lost. In consequence, pressure pulsations in the large arteries are increased, and flow pulsations extend more peripherally into small fragile arteries of organs with high resting blood flow, notably the brain and kidney. Ill effects on the heart include increased left ventricular (LV) pressure during systole with greater oxygen demand, and left ventricular hypertrophy (LVH) with predisposition to systolic and diastolic heart failure.

Decreased aortic pressure throughout diastole (and abbreviation of diastolic period in LVH) limits capacity for coronary perfusion and predisposes to myocardial ischaemia. Ill effects on large arteries include faster development of atherosclerotic plaques in coronary and cerebral arteries from increased pulsatile stress and altered endothelial shear stress, accelerated development of aneurysms at points of weakening (branching) in the cerebral circulation, atherosclerotic degeneration of the infra-renal aorta from increased pulsatile shear at the endothelium and radial stress in the media.

Ill effects on the microcirculation in brain and kidney are attributable to high pulsatile flow extending into these vessels, leading to medial disruption with micro-haemorrhage, and to endothelial damage and thrombosis with microinfarcts.

Despite the complexity of underlying mechanisms, and the importance of their consequences, clinical hemodynamic assessment of patients with disease, and evaluations of subjects without disease are made almost exclusively with the cuff sphygmomanometer, also known as the brachial cuff, applied to the upper arm. This process has not changed in the past century. Over one hundred years ago, before the brachial cuff was introduced, clinical information was sought from interpretation of pulse wave contours. This practice lapsed with introduction of the cuff, but has recently been revived with development of arterial tonometry.

Proponents of arterial tonometry have shown that features of the arterial pressure waveform do provide prognostic information which is incremental to that provided by cuff sphygmomanometric numbers of brachial systolic, diastolic, and pulse pressure. This has been shown for augmentation of the central (aortic or carotid) pressure pulse and for amplification of the pressure pulse between the aortic and upper limb arteries.

Advances in this field are limited by difficulties in analysis of the pressure waveforms. Measurement of late systolic augmentation is dependent on identification of the initial peak created by ventricular ejection, and its separation from the beginning of the reflected wave. Measurement of amplification is dependent on assessment of central and peripheral pressure waveforms, measured separately, or on the generation of the central waveform from the peripheral waveform, assuming a generalised transfer function or through assuming identity of mean and diastolic pressure in central and peripheral arteries.

A simplified method for pulse wave analysis, which is independent of such factors, is highly desirable, if this field is to advance. It is also desirable that such a method be independent of blood pressure cuff calibration. In major drug studies published to date, effects of pulsatile pressure change at the heart have been assessed from central systolic and pulse pressure, calibrated from brachial cuff pressure.

Errors in measurement of brachial systolic and diastolic pressure are well known, with the US standard (AAMI SP10) accepting mean offset and standard deviation respectively of $\leq 5$ mmHg and $\leq 8$ mmHg in equivalence comparisons. No such equivalence comparisons have been published for pulse pressure, but differences are likely to compound those for systolic and diastolic pressure. In comparisons of predictors of LV mass in treatment of hypertension, cuff pressures were of far less value than indices determined from the pressure waveform alone.

DISCLOSURE OF INVENTION

It is an object of the present invention to provide a method of determining ageing effect and cardiovascular risk in humans that overcomes the problems of identifying augmentation and of measuring amplification in prior art methods, and is independent of cuff pressure.

It is another object of the present invention that such a method be based on the comparison of harmonic components of the peripheral and central pressure, flow, diameter or volume pulse.

It is a preferred object of the invention that the comparison be of the lowest harmonic values against one or more of the higher harmonic values.

The present invention makes use of the fact that, in fully grown human adults, there are consistent relationships between waveforms of pressure, flow, volume and diameter at the heart and in the upper body arterial vessels that can be expressed in terms of frequency components and transfer functions.

As a consequence of ageing and disease, there are changes in properties of the aorta and arteries in the lower body which alter ascending aortic impedance and left ventricular load. These can be interpreted from arterial pulse waveforms in the arms, neck and upper body.

Despite changes in aortic impedance with age and disease, the ascending aortic flow waveform remains basically similar, with forward flow in the first third to half of the cardiac cycle, and with no flow in the second two thirds to last half of the cardiac cycle. In consequence of this, amplitude of the first harmonic dominates all higher harmonics.

Arterial changes with ageing, hypertension and disease lead to substantial increase in modulus (also referred to as amplitude) of ascending aortic impedance at normal heart rate frequency (50 to 120 cycles/min; 0.8 to 2.0 Hz). These changes result in the progressive dominance of lower (first and second) harmonics of the pressure pulse at normal heart rate frequency.

It has been found that adverse changes can be interpreted from relative amplitude of harmonic (frequency) components of the ascending aortic pressure pulse and, in consequence, from relative amplitude of frequency components of pressure, diameter, flow and volume pulses in the upper body, including neck, arms and fingers.

Adverse effects of ageing and disease on the heart and circulation are magnified when relative amplitude of the first harmonic of flow over higher harmonics is increased by left ventricular hypertrophy or increase in heart rate, where duration of ejection approaches 50% (from 33%) of the cardiac cycle. Such change can be interpreted from waveform changes in upper body arteries.

Adverse effects of age and disease are magnified by central cardiac and peripheral arterial damage when the first harmonic of the aortic pressure wave is increased. Hence a power spectra (e.g. modulus squared) can be more useful than modulus alone to identify the changes and effects.

It has also been found that phase difference between harmonics alters shape of the pressure wave. Hence it is yet another object of the invention to include an assessment of relative differences in phase in the method of determining ageing effect and cardiovascular risk in humans.

Accordingly, the present invention provides a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the amplitude based value of the first harmonic ($H_1$) to the amplitude based value of a selected higher harmonic ($H_N$) to provide an index of arterial ageing, and (iv) comparing the index to normative values of index of arterial ageing to determine ageing effect and cardiovascular risk.

Preferably, the index is site specific, and the amplitude based values of the harmonics include the raw value of the amplitude, the squared value of the amplitude, and the product value of the amplitude with the cosine of the phase $\phi$ of the harmonic having the amplitude.

Preferably, the pulse waveform is from the neck, arms or fingers of the patient.

It is preferred that the pulse waveform is selected from the group consisting of pressure, flow, diameter and volume waveform.

In a preferred form, the frequency dependent components of the pulse waveform are extracted by Fourier Analysis.

According to one particular aspect of the present invention there is provided a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the amplitude of the first harmonic ($H_1$) to any one or the sum of the amplitudes of a selected plurality of the second and subsequent harmonics ($H_2 \ldots H_N$) to provide a first index of arterial ageing, and (iv) comparing the first index to normative values of index of arterial ageing to determine ageing effect and cardiovascular risk.

Preferably, the ratio of the amplitude of the first harmonic ($H_1$) to the sum of the amplitudes of the second and subsequent harmonics ($H_2 \ldots H_N$) is determined to provide the first index by using the formula:

$$\frac{H_1}{\Sigma\{H_2 + H_3 + H_4 \ldots H_N\}},$$

and wherein N is a frequency of between 6 to 12 Hz.

According to another particular aspect of the present invention there is provided a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the square of the amplitude of the first harmonic ($H_1$) to the square of any one or to the sum of the squares of the amplitudes of a selected plurality of the second and subsequent harmonics ($H_2 \ldots H_N$) to provide a second index of arterial ageing, and (iv) comparing the second index to normative values of index of arterial ageing to determine ageing effect and cardiovascular risk.

Preferably, the ratio of the square of the amplitude of the first harmonic ($H_1$) to the sum of the squares of the amplitudes of a selected plurality of the second and subsequent harmonics ($H_2 \ldots H_N$) is determined to provide the second index by using the formula:

$$\frac{H_1^2}{\Sigma\{H_2^2 + H_3^2 + H_4^2 \ldots H_N^2\}}$$

According to yet another particular aspect of the present invention there is provided a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the product of the amplitude of the first harmonic ($H_1$) with the cosine of the phase $\phi$ of $H_1$ to the product of the amplitude of any one or to the sum of the products of the amplitudes of a selected plurality of the second and subsequent harmonics ($H_2 \ldots H_N$) with the cosine of the phase $\phi$ of the or each harmonic to provide a third index of arterial ageing, and (iv) comparing the third index to normative values of index of arterial ageing to determine ageing effect and cardiovascular risk.

Preferably, the ratio of the product of the amplitude of the first harmonic ($H_1$) with the cosine of the phase $\phi$ of $H_1$ to the sum of the products of the amplitudes of a selected plurality of the second and subsequent harmonics ($H_2 \ldots H_N$) with the cosine of the phase $\phi$ of the or each harmonic is determined to provide the third index by using the formula:

$$\frac{H_1 \cos\phi_1}{\Sigma\{H_2 \cos\phi_2 + H_3 \cos\phi_3 + \ldots\}}$$

The present invention also provides a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the sum of the amplitudes of the first and second harmonics to the sum of the amplitudes of a selected plurality of the third and subsequent harmonics ($H_3 \ldots H_N$) to provide a fourth index of arterial ageing by using the formula:

$$\frac{H_1 + H_2}{\Sigma\{H_3 + H_4 \ldots H_N\}}$$

and, (iv) comparing the fourth index to normative values of index of arterial ageing to determine ageing effect and cardiovascular risk.

The present invention further provides a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the sum of the squares of the amplitudes of the first and second harmonics to the sum of the squares of the amplitudes of a selected plurality of the third and subsequent harmonics ($H_3 \ldots H_N$) to provide a fifth index of arterial ageing by using the formula:

$$\frac{H_1^2 + H_2^2}{\Sigma\{H_3^2 + H_4^2 \ldots H_N^2\}}$$

and, (iv) comparing the fifth index to normative values of index of arterial ageing to determine ageing effect and cardiovascular risk.

The present invention still further provides a method of determining ageing effect and cardiovascular risk in a human patient comprising:

(i) measuring the arterial pulse waveform of the patient when the heart is beating regularly, (ii) extracting the frequency dependent components of the pulse waveform, (iii) determining the ratio of the sum of the products of the amplitude of each of the first and second harmonics with the cosine of the phase $\phi$ of the first and second harmonics respectively to the sum of the products of the amplitude of each of a selected plurality of the third and subsequent harmonics ($H_3 \ldots H_N$) with the cosine of the phase $\phi$ of the respective third and subsequent harmonics to provide a sixth index of arterial ageing by using the formula:

$$\frac{H_1 \cos\phi_1 + H_2 \cos\phi_2}{\Sigma\{H_3 \cos\phi_3 + H_4 \cos_4 \ldots\}}$$

and, (iv) comparing the sixth index to normative values of index of arterial ageing to determine ageing effect and cardiovascular risk.

Preferably, the amplitude based values of the harmonics are measured by tonometric pressure, phase locked echo tracking diameter, Doppler flow or finger plethysmogram.

It is preferred that the index is used to assess a patient's response or potential response to drug therapy.

In a still further preferred form, the amplitude based value of a harmonic number is replaced by a corresponding frequency band.

The methods of the present invention also provide means for determining the beneficial effect of drugs on ascending aortic impedance based on the harmonic moduli of upper body pulse waveforms.

The methods of the present invention may also provide a better prognosis of risk of cardiovascular disease (such as stroke, heart attack and heart failure) with the effect of ageing based on assessment of the shape of the waveforms and comparison with a normative index.

One aspect of the method includes the effects of phase ($\phi$) by using the formula:

$$\frac{H_1 \cos\phi_1}{\Sigma\{H_2 \cos\phi_2 + H_3 \cos\phi_3 + \ldots\}}$$

This may be particularly useful where pressure and flow are measured together for determination of vascular impedance. Note that $\phi$ is a measure of time of delay in the starting points of any two harmonics.

The methods of the invention all include the step of determining the ratio of various amplitude based values (derived by various mathematical treatments of the harmonics), but all depend on dominance of lower over higher harmonics with increased age and cardiovascular risk.

The methods of the present invention may be carried out by information processing means, such as computers.

BRIEF DESCRIPTION OF THE DRAWINGS

In order that the invention may be more readily understood and put into practical effect, reference will now be made accompanying drawings, which are summarised as follows.

FIG. 5b is a graph showing modulus squared plotted against frequency for the data shown in FIG. 5a.

FIG. 10a shows ascending aortic impedance in a group of patients before and after administration of sublingual nitroglycerin.

FIG. 10b shows the effect of nitroglycerin on apparent phase velocity in the proximal aorta.

FIGS. 11a-11f show the effects of vasodilator therapy on aortic input impedance moduli in humans.

MODES FOR CARRYING OUT THE INVENTION

Pathophysiologic Mechanisms

Figure 1A:
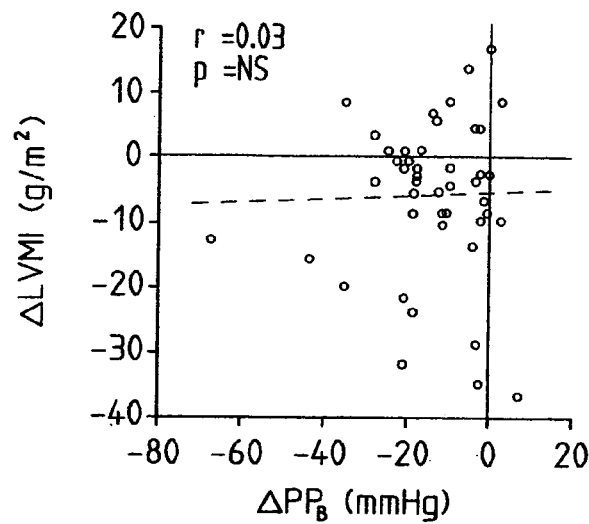
FIG. 1a shows the relationship between change in left ventricular mass as a surrogate of mortality and change in brachial cuff pulse pressure.
Figure 1B:
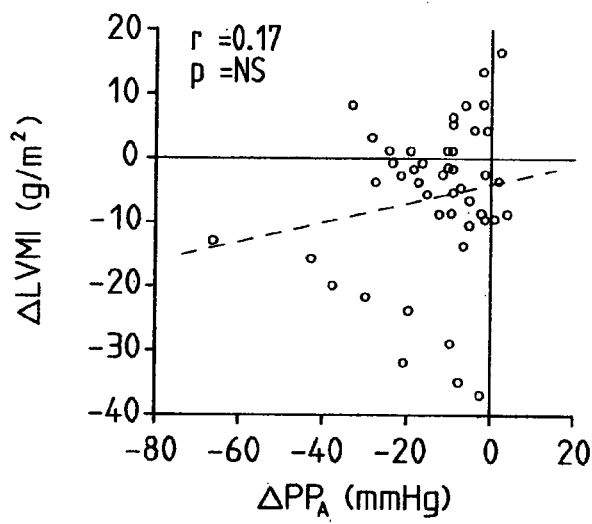
FIG. 1b shows the relationship between change in left ventricular mass as a surrogate of mortality and aortic pulse pressure.
Figure 1C:
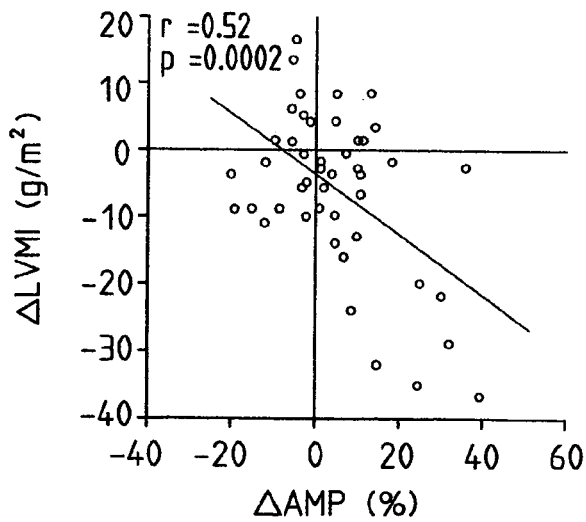
FIG. 1c shows the relationship between change in left ventricular mass as a surrogate of mortality and pressure wave amplification between aortic to radial artery.

FIGS. 1a to 1c show the relationship between change in left ventricular mass as a surrogate of mortality and change in brachial cuff pulse pressure (FIG. 1a), aortic pulse pressure (FIG. 1b) and pressure wave amplification between aorta to radial artery (FIG. 1c). In these Figures the axes are:

LVM1=left ventricular mass index (for body size)
$PP_B$=brachial cuff pulse pressure
AMP=amplitude
R=slope
P=level of significance (statistical determination)

As can be seen from FIGS. 1a to 1c, cuff pressure and aortic pulse pressure (FIGS. 1a and 1b) were of less value than the indices determined from pressure waveform (FIG. 1c).

Figure 2:
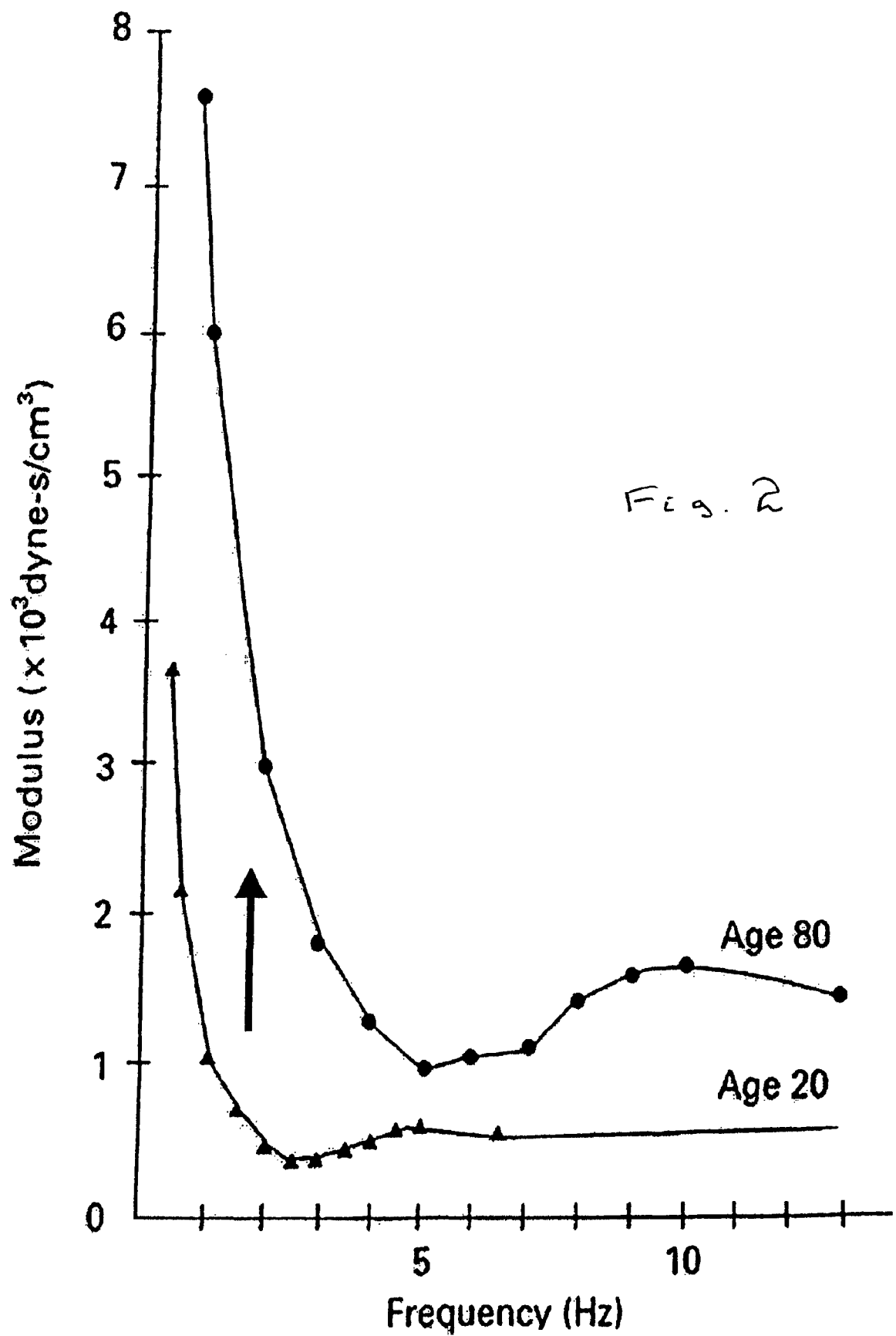
FIG. 2 shows aortic impedance at age 20 and age 80.

Aortic stiffening with age is known to have two adverse effects on ascending aortic impedance. Stiffening of the proximal aorta increases characteristic impedance (Zc), about which impedance fluctuates, while early return of wave reflection increase the frequency at which fluctuations occur. The summed effect for a two-fold increase in Zc and aortic pulse wave velocity (PWV) is a four-fold increase in impedance at heart rate frequency. Progressively lesser differences are seen at higher frequencies (FIG. 2).

Figures 3A, 3B:
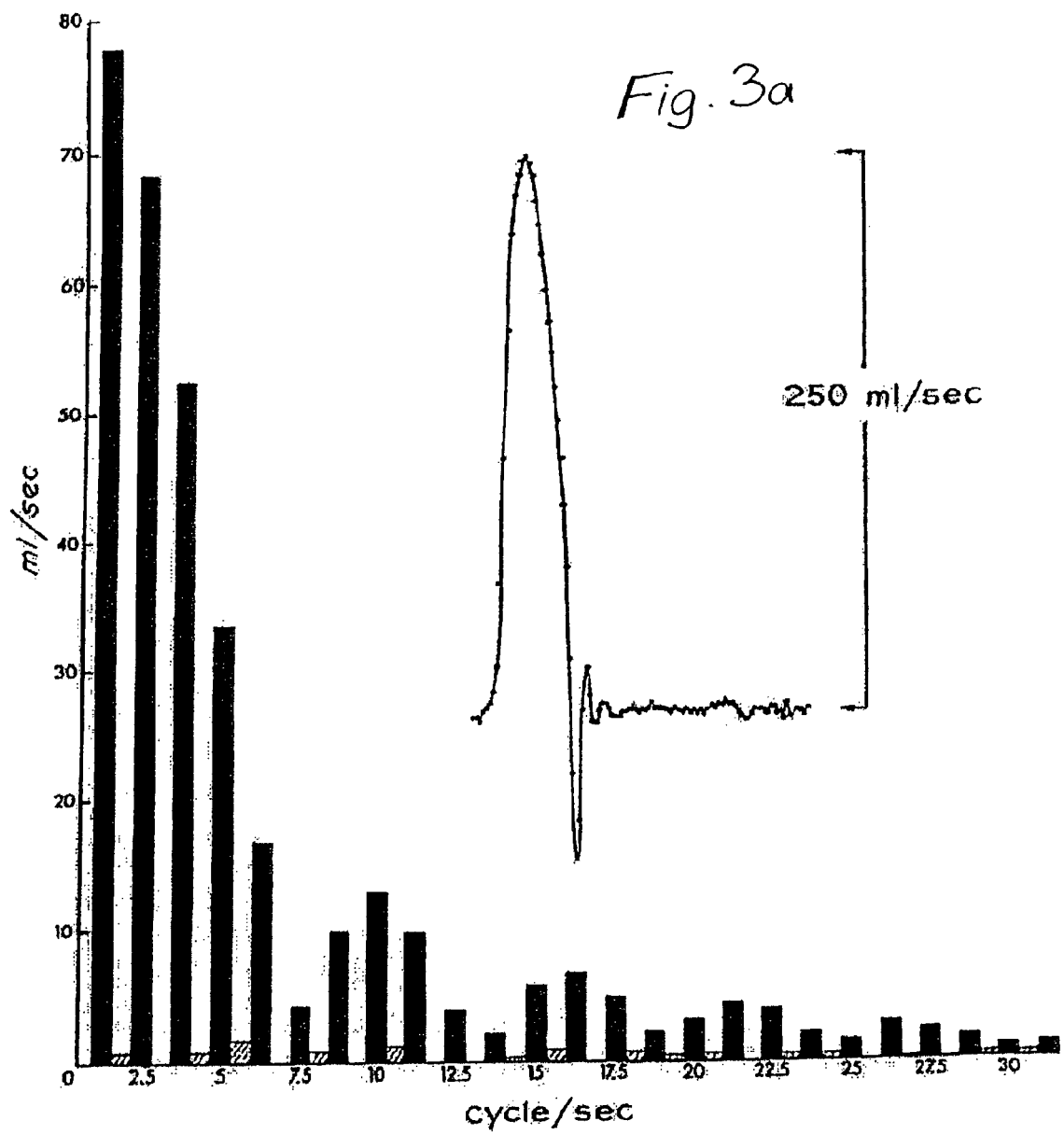
FIG. 3a is a flow wave recorded in the ascending aorta of a 17.9 kg dog and plotted from a digital voltmeter output, with the heart rate at 1.25/second.
FIG. 3b is a graph derived from the flow wave of FIG. 3a showing the first 26 harmonics after correcting each for instrumental errors, the approximate noise level being indicated by the small diagonally striped bars which were obtained by submitting the diastolic part of the wave to Fourier Analysis.
Figure 4:
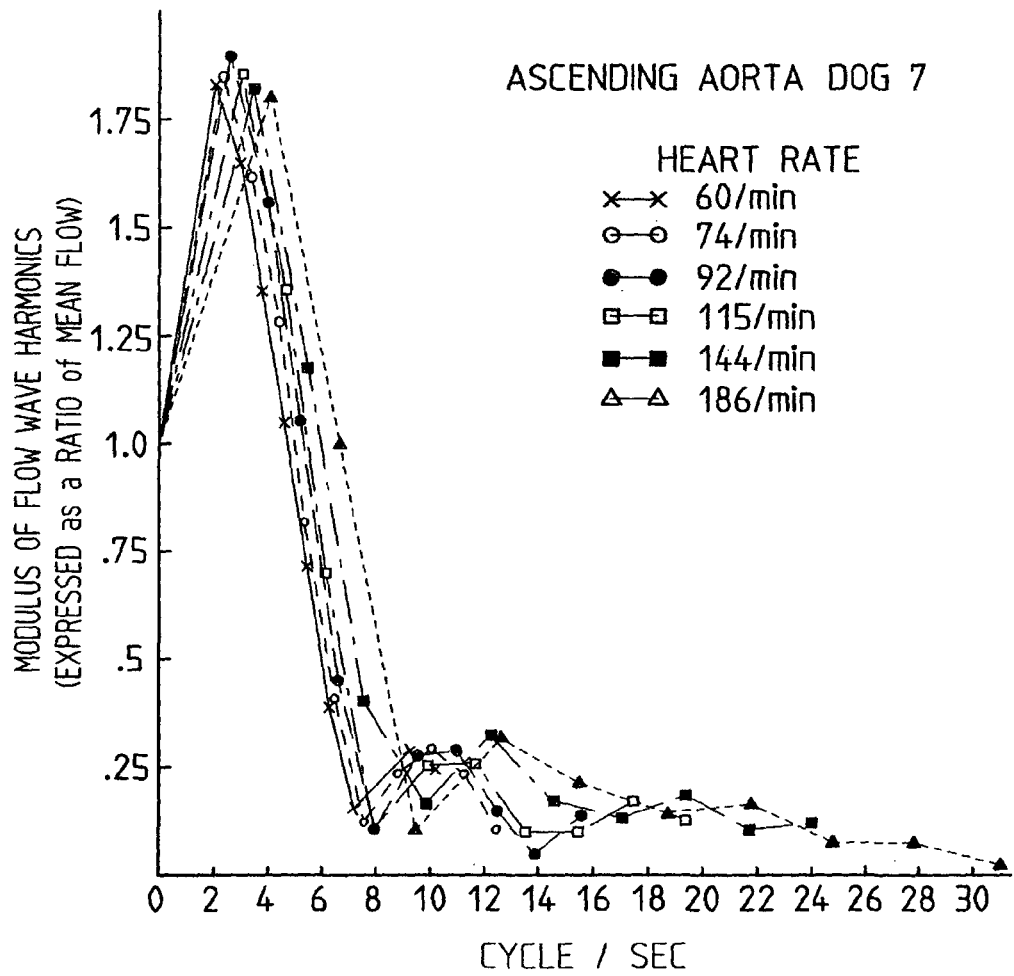
FIG. 4 shows the moduli of the first 10 harmonics of the ascending aortic flow waves at heart rates between 60 and 186 per minute, each point being the average of 5 waves, with standard error not being plotted since it was extremely small, there being little difference in the shape of the waves at the same frequency, the data being obtained from a 7.9 kg dog which had a surgically induced heart block and an artificially paced heart.

Amplitude of ascending aortic pressure wave harmonics is dependent on impedance and on amplitude of the ascending aortic flow wave generated by ventricular ejection. Normally, the first harmonic of flow is dominant over all others (FIGS. 3a and 3b). The largest amplitude (measured by velocity) in FIG. 3b is derived from the most dominant or first harmonic. Hence the first harmonic of pressure is utterly dominant in older persons (FIG. 5a) though still being relatively high in the young. Relative dominance of the first harmonic of flow is greater at high heart rates (FIG. 4). In young persons, particular for heart rates appropriate for exercise (over 100/min) the minimal value of ascending aortic impedance modulus corresponds to the first and second harmonics of flow, while the third and higher harmonics of flow occur at frequencies where impedance modulus is somewhat greater (FIG. 2).

Implication of change in impedance phase need not be considered in preliminary analysis, but may be relevant in detailed application of embodiments of the invention.

Dominance of the lower harmonics of pressure in older persons is thus a consequence of ascending aortic impedance change with age. It embraces the combined effects of local aortic stiffening and the ill effect of early wave reflection. It is logical to utilise this as a measure of arterial efficiency. Such a view is enhanced by the following considerations:

1. Pressure Wave Pattern

Figure 5A:
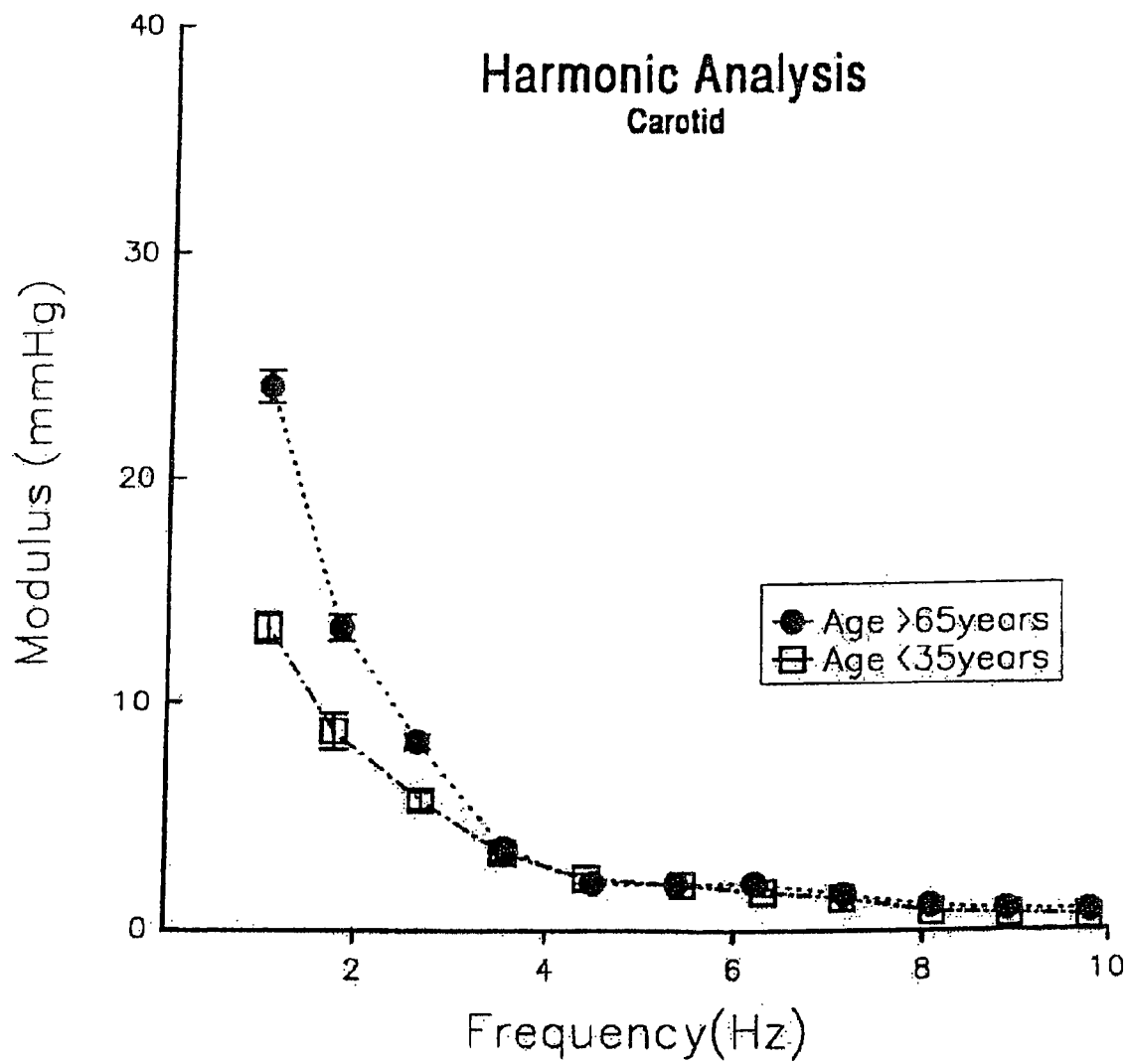
FIG. 5a shows a comparison of carotid pressure harmonic components between young and old people from a fundamental frequency to 10 Hz using arterial applanation tonometry values in mmHg.

As shown in FIG. 5a, in old people, the first harmonic dominates over all other harmonics whereas in young people the amplitude of the first harmonic is far less.

For example, for people older than 65 years of age, the amplitude of the first harmonic (modulus approximately 25 mm Hg) is compared to the amplitude of the fifth harmonic (modulus approximately 3 mm Hg) in the form of a ratio to provide an index of approximately 8.33.

The same comparison is conducted for people younger than 35 years of age to provide an index of approximately 4.33.

For each age group, a comparison of the derived index against normative values of an index of arterial ageing can be conducted to determine ageing effect and cardiovascular risk. This is carried out by information processing means.

Figure 5B:
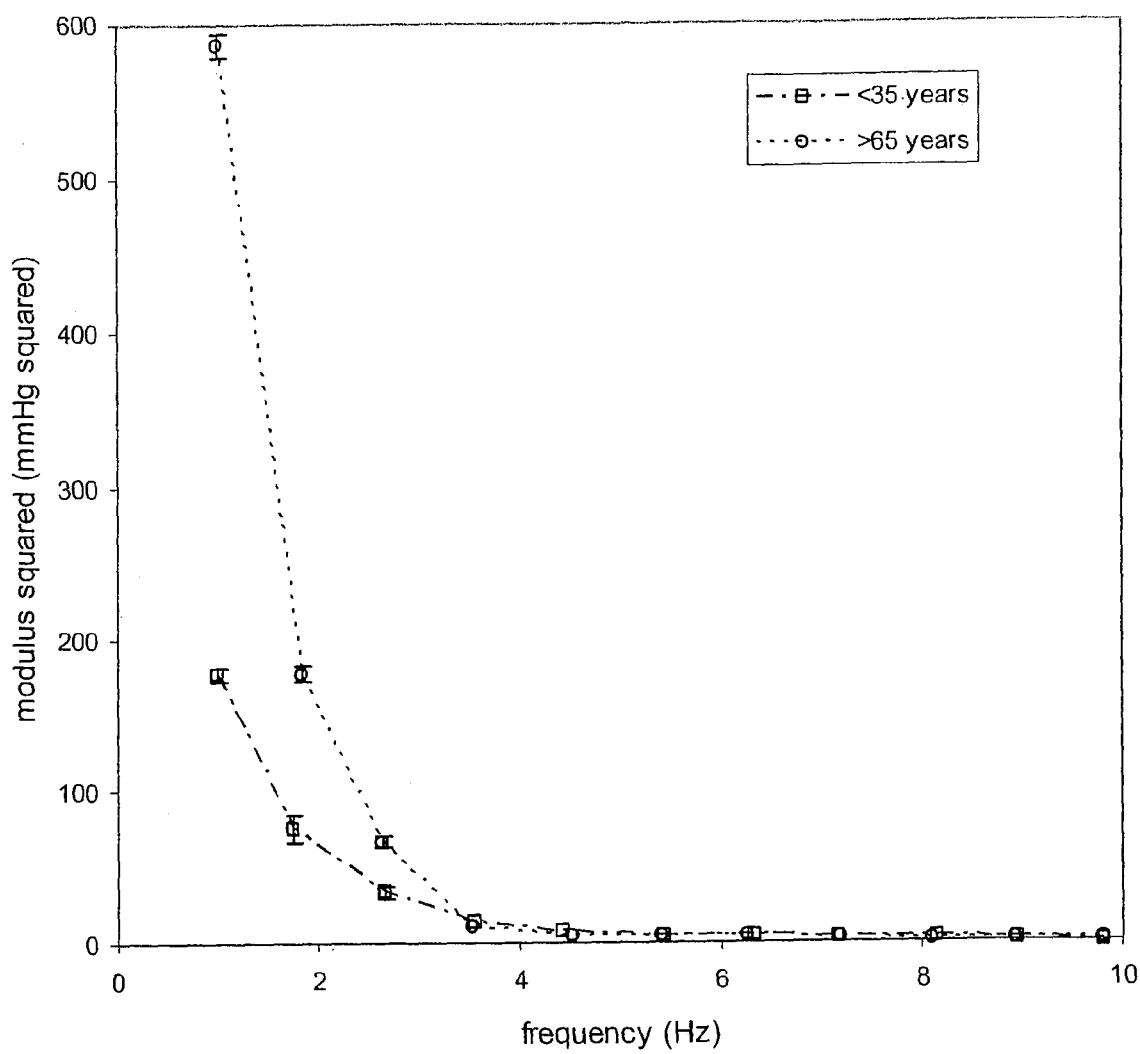

FIG. 5b shows modulus squared (as the amplitude based value) plotted against frequency for the data shown in FIG. 5a. The same comparisons as conducted above with reference to FIG. 5a can be conducted with reference to FIG. 5b to provide indexes and to compare those derived indexes against normative values of an index of arterial ageing.

Figure 5C:
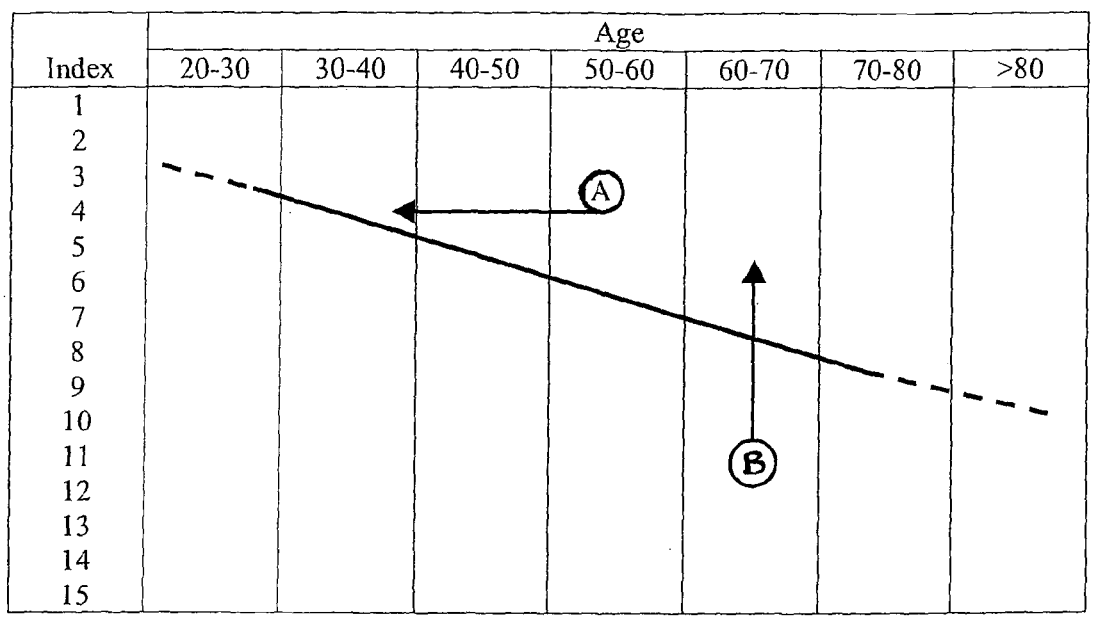
FIG. 5c shows a table of index values for a series of age groups, with a line through the table distinguishing between index values representing generally lower than normal ageing effect and cardiovascular risk (above the line) and index rates representing generally higher than normal ageing effect and cardiovascular risk (below the line), and with the line signifying normative values of index derived from determining the ratio of $H_1$ to $H_3$.

Examples of such comparisons against normative values of an index of arterial ageing are shown in FIG. 5c, which represents a table of index values versus age groups and is based on the data in FIG. 5a. A line through the table distinguishes between index values representing generally lower than normal ageing effect and cardiovascular risk (above the line) and index values representing generally higher than normal ageing effect and cardiovascular risk (below the line), with the line signifying normative values of index derived from determining the ratio of $H_1$ to $H_3$. The table shows that a 54 year old person's derived index of about 4 is indicative of younger arteries normal for a person in their mid thirties (see arrow A). The table also shows the beneficial effect of treatment in a 65 year old person whose derived index is reduced to about 5 from an earlier index of about 11 (see arrow B).

Another benefit of comparing the derived index against normative values of an index of arterial ageing and against the patient's earlier derived index is to assess the efficacy of drug treatment or therapy.

It will be understood that the amplitude of the first harmonic (derived by Fourier Analysis) is from a single sine wave (over a period), the amplitude of the second harmonic (also derived by Fourier Analysis) is from two sine waves over the same period, the amplitude of the third harmonic (also derived by Fourier Analysis) is from three sine waves over the same period, and so on for each subsequently higher harmonic.

Figure 6:
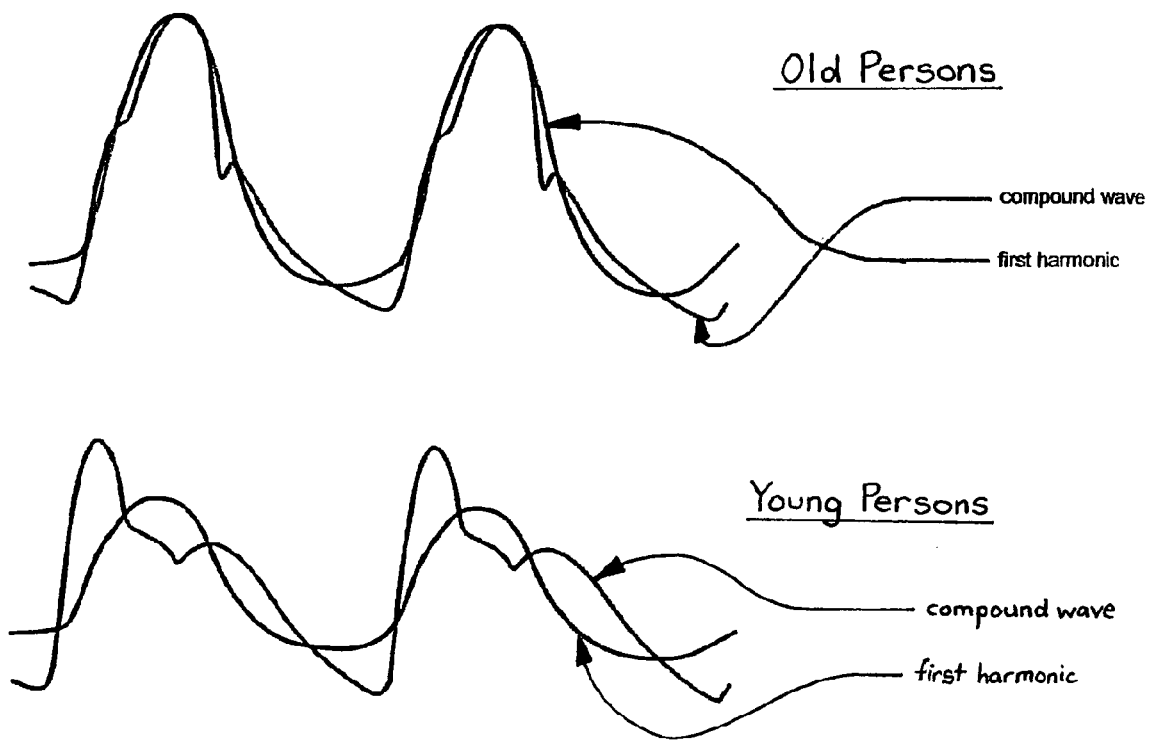
FIG. 6 shows the first harmonic of the pressure pulse and the compound wave for old persons and young persons.

Change in the pressure wave pattern in central and peripheral arteries with age is dominated by early return of wave reflection and merging of the secondary reflected wave with the systolic part of the wave. The dominance of the first pressure harmonic in older persons is most apparent when one considers a train of waves rather than a single pulse (FIG. 6). These considerations apply to central and peripheral pressure waves, though they are most apparent in the central pressure waves.

2. Flow Wave Pattern

Figure 7:
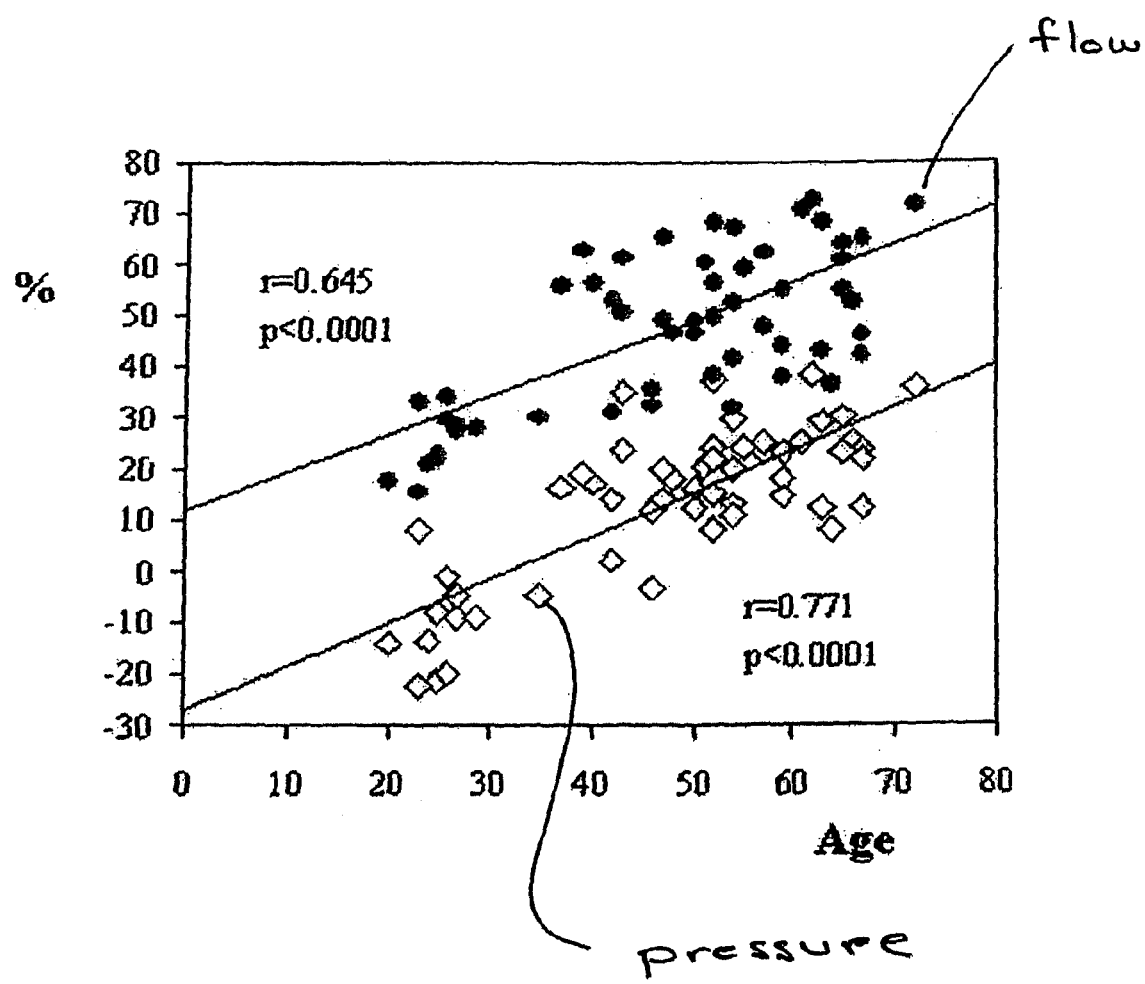
FIG. 7 is an augmentation index for carotid pressure and flow indicating a similar relationship with age.
Figure 8:
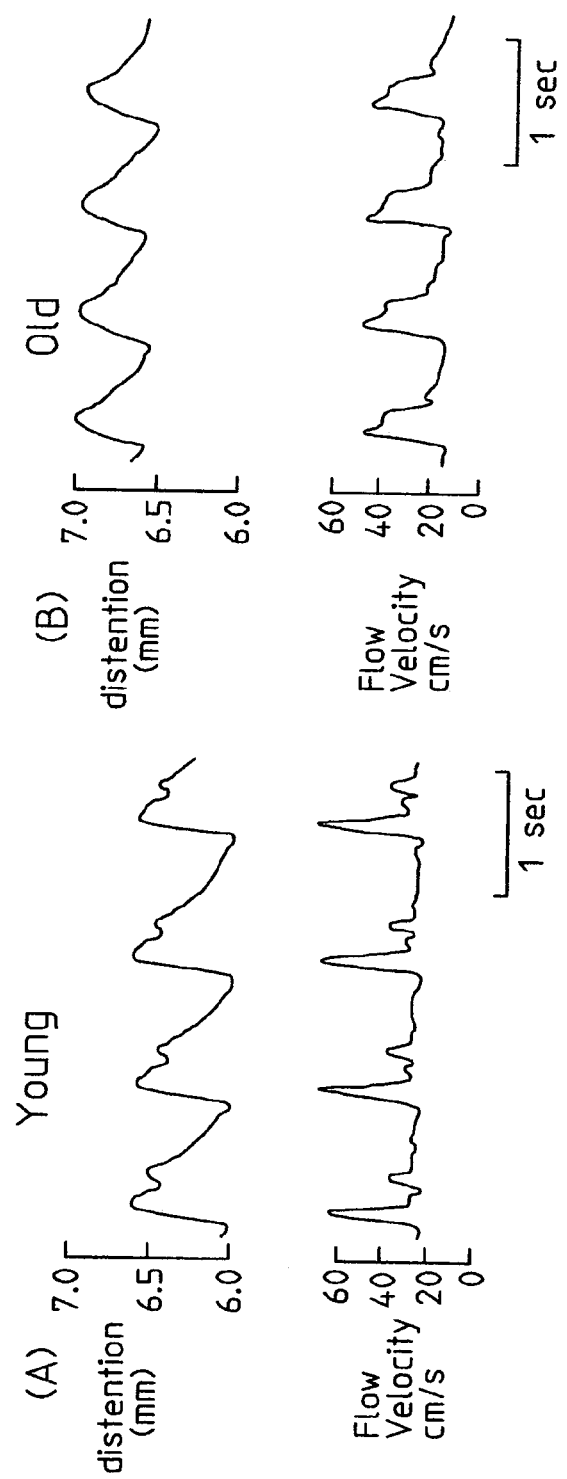
FIG. 8 shows the amplitude of secondary flow waves in the carotid artery which increases substantially with age.

Increase in cerebral flow pulsation with age is due to and assessable from increase in the first harmonic of pressure. This is apparent as similar increase in flow with pressure augmentation in the internal carotid artery with age (FIG. 7) as well as from the waveform itself (FIG. 8). High harmonics of the waveform appear to be attenuated in the large cerebral arteries, with principally the first harmonic propagated into and through the small fragile cerebral vessels where age-related "pulse wave encephalopathy" is seen.

Increase in amplitude of the first harmonic of the carotid flow pulsations is clearly deleterious with respect to cerebral micro vessels.

3. Left Ventricular Performance

Figure 9:
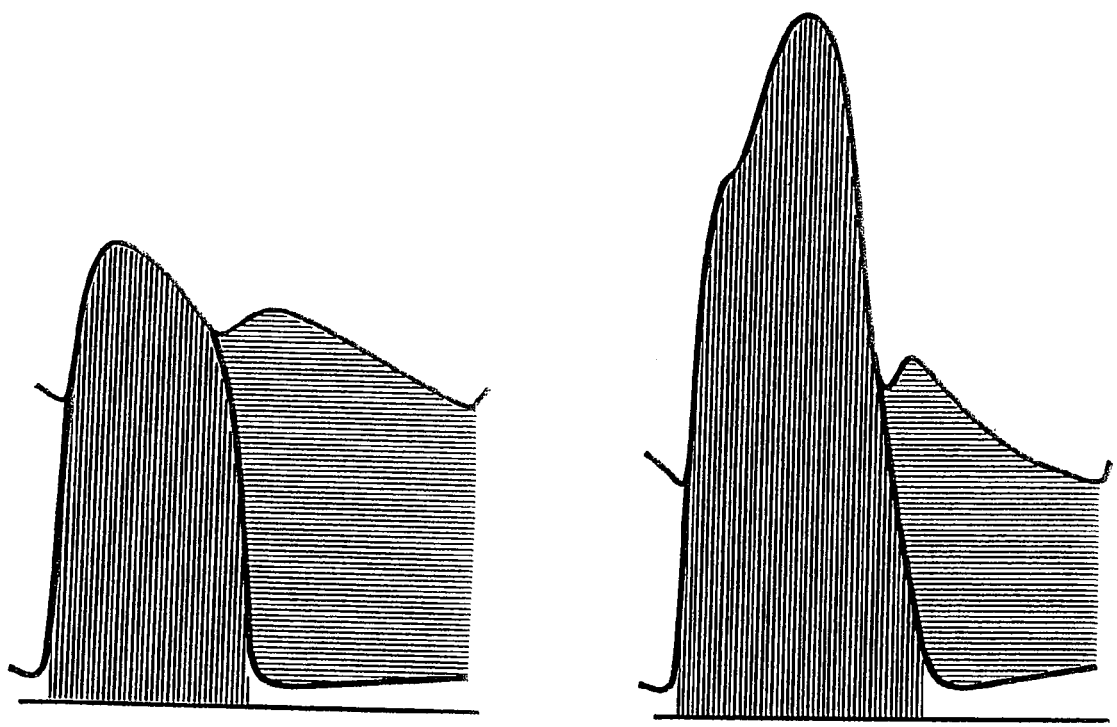
FIG. 9 shows the aortic and left ventricular pressure valves in young people (left) and old people (right).

Design of the arterial system is optimised by minimising pressure rise during systole and pressure fall during diastole. This is most important during activity when heart rate is relatively high (>100 beats/min), and where the period of systole is approximately the same as the period of diastole. With ageing, the worst case is approached, where during activity, the pressure during systole is very high and the pressure during diastole is very low (FIG. 9).

4. Effects of Vasodilator Drugs on Ascending Aortic Pressure

FIG. 10a shows ascending aortic impedance in a group of patients before and after administration of sublingual nitroglycerin suggesting a decrease in peripheral wave reflection without a change in arteriolar tone or in the properties of the proximal aorta.

FIG. 10b shows the effect of nitroglycerin on apparent phase velocity in the proximal aorta, the first and second harmonics being reduced by nitroglycerin.

Figure 10C:
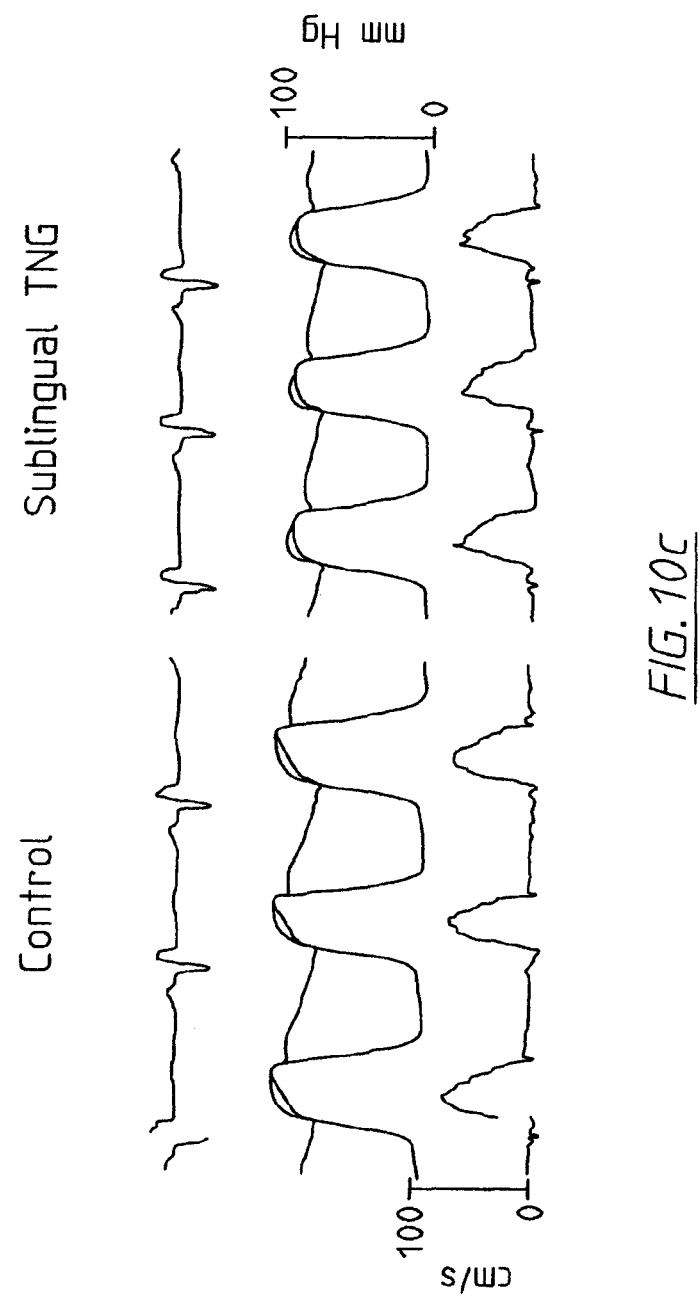
FIG. 10c shows representative left ventricular and aortic pressure tracings together with ascending aortic flow velocity in a patient with angina pectoris before (left) and after (right) administration of sublingual nitroglycerin.

FIG. 10c shows representative left ventricular and aortic pressure tracings together with ascending aortic flow velocity in a patient with angina pectoris before (left) and after (right) administration of sublingual nitroglycerin.

By comparing the pressure waveform (middle) in the aorta with the flow waveform (bottom) in the aorta, the ascending aortic impedance can be assessed, which is the modulus of pressure over the modulus of flow.

Figure 12:
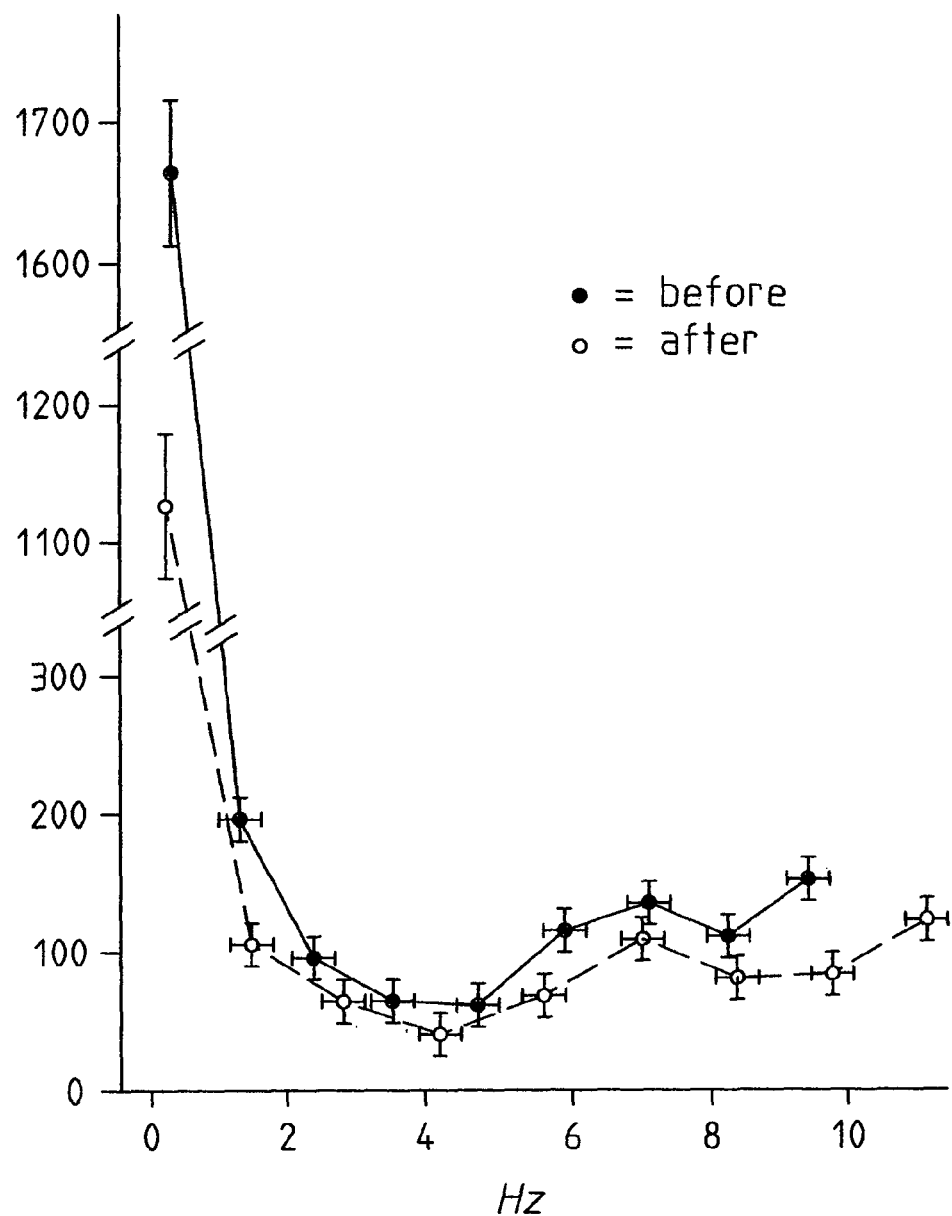
FIG. 12 shows the ascending aortic impedance before (closed circles) and after (open circles) nifedipine treatment.

FIGS. 11a-11f show the effects of vasodilator therapy on aortic input impedance moduli in humans. The reduction in low-frequency impedance moduli that was invariably seen can be attributed to decrease in wave reflection and is responsible for a reduction in left ventricular afterload. In particular:

FIG. 11a is heart failure: pre and post nitroprusside.
FIG. 11b is coronary disease: pre and post nitroprusside.
FIG. 11c is heart failure: pre and post nitroprusside.
FIG. 11d is hypertensive: pre and post nitroprusside.
FIG. 11e is hypertensive: pre and post nitroprusside.
FIG. 11f is heart failure: pre and post dobutamine.
FIG. 12 shows the ascending aortic impedance before (closed circles) and after (open circles) nifedipine.

Drugs such as nitroglycerin have the most prominent effect on the lowest frequency components of impedance, and their least effect on the highest frequency components (FIGS. 10,11 and 12). The therapeutic effect of lowering pressure in late systole is attributable to reduction in amplitude of the first harmonic of pressure, not on higher harmonics. Hence, beneficial effects of such therapy can be assessed from reduction in the first harmonic compared to the higher harmonics.

Figure 13:
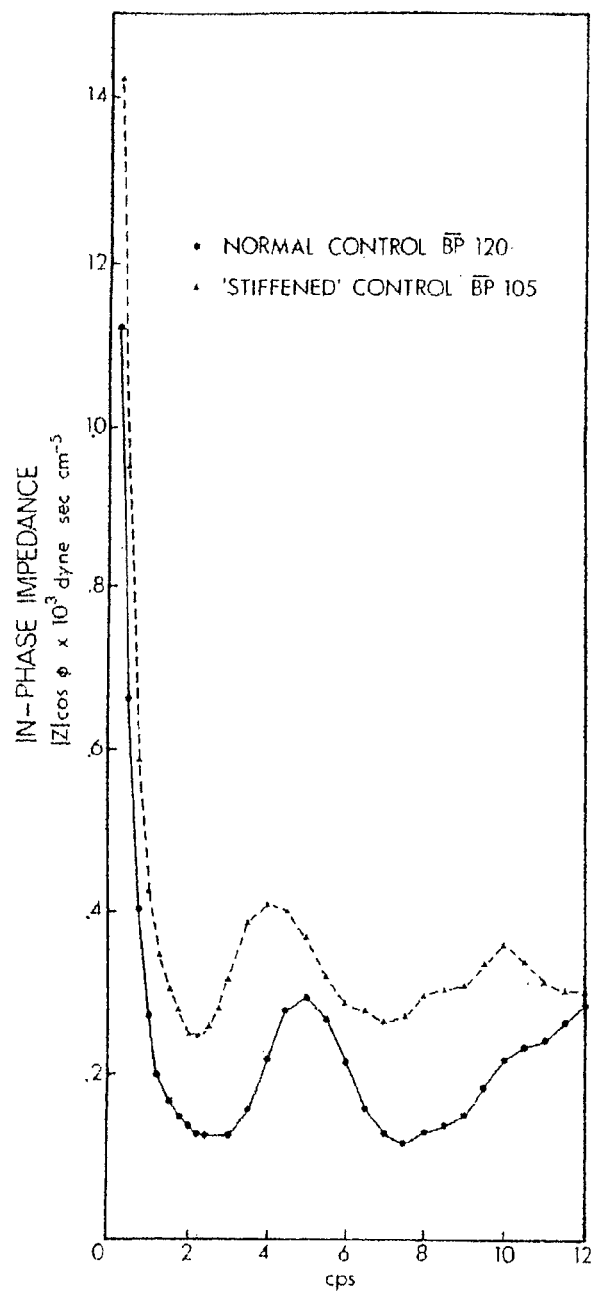
FIG. 13 is a graph showing aortic in-phase impedance (impedance modulus (z) multiplied by cosine of impedance phase angle φ) plotted against frequency for a dog before and after application of rigid sleeves around the proximal part of the aorta.

FIG. 13 shows aortic in-phase impedance (the product of impedance modulus (z) with the cosine of impedance phase angle $\phi$) plotted against frequency for a dog before and after application of rigid sleeves around the proximal part of the aorta, the sleeves simulating the stiffening of the aorta with age. In-phase impedance (z cosine $\phi$) is the major determination of pulsatile energy losses in the systemic circulation, and is increased when the aorta stiffens with age.

5. Exponential Ill Effects

The exponential increase in cardiovascular events with age (around 8-fold between 50 and 80 years), and with increase in blood pressure (around 4-fold for systolic blood pressure between 120 and 160 mmHg) can be explained on the basis of the multiple ill effects of early wave reflection on the heart and microvasculature of brain and kidney. Use of power spectra, as opposed to harmonic amplitudes, may better delineate these increases.

Thus, the invention provides better characterisation of ageing effect and cardiovascular risk independent of brachial cuff calibration values, and independent of contemporary analysis of pulse waveform as augmentation or amplification. The analysis is based on previously described theoretical and pathophysiological mechanisms, and emphasises the hazards when the first harmonic of the arterial wave dominates over other harmonics at rest or exercise. Hazard is dependent on the degree of domination, and applies to central and peripheral pulses, and to pressure, diameter, volume and flow pulses.

The arterial ageing index has a numerical value that is specific for parameter measured (pressure, diameter, volume, flow) and to site in the upper body. Normative (normal) values of index for each parameter and site will be established, as they have been for brachial systolic pressure, augmentation index etc. Risk will be established from data in clinical trials, as will change in risk with vasoactive therapy given to alter the arterial ageing index.

Reference to harmonics rather than frequency is made to explain mechanisms when the heart is beating regularly. The same principles however apply when the heart is beating irregularly, or when regular heart rate varies over a long period of time that includes rest, exercise and arousal. Hence the same information can be applied by comparing the relationship of low frequency to high frequency components, eg 0.8 to 2.0 hz compared to >2hz, when waveform components are recorded as a frequency spectrum.

Various modifications may be made in details of the above described methods for characterisation of ageing effect and cardiovascular risk without departing from the scope and ambit of the invention.

The invention claimed is:

1. A method of determining ageing effect and cardiovascular risk in a human patient comprising:
    (i) measuring an arterial pulse waveform of the patient when the patient's heart is beating regularly,
    (ii) extracting frequency dependent components of the pulse waveform,
    (iii) determining a ratio of an amplitude based value of a first harmonic ($H_1$) to an amplitude based value of a selected higher harmonic relative to the first harmonic to provide a first index of arterial ageing,
    (iv) determining a ratio of a product of an amplitude of $H_1$ with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide a second index of arterial ageing, and (v) comparing the first and second indexes to normative values of an index of arterial ageing to determine ageing effect and cardiovascular risk.

2. The method according to claim 1 wherein the first index is site-specific, and the amplitude based values of the harmonics include a raw value of a particular amplitude, a squared value of the particular amplitude, and a product value of the particular amplitude with a cosine of a phase $\phi$ of a harmonic having the particular amplitude.

3. The method according to claim 1 wherein the pulse waveform is from the neck, arms or fingers of the patient.

4. The method according to claim 1 wherein the pulse waveform is selected from a group consisting of pressure, flow, diameter and volume waveform.

5. The method according to claim 1 wherein the frequency dependent components of the pulse waveform are extracted by Fourier Analysis.

6. A method of determining ageing effect and cardiovascular risk in a human patient comprising:
(i) measuring an arterial pulse waveform of the patient when the patient's heart is beating regularly,
(ii) extracting frequency dependent components of the pulse waveform,
(iii) determining a ratio of an amplitude of a first harmonic ($H_1$) to any one or a sum of amplitudes of a selected plurality of a second and subsequent harmonics ($H_2 \ldots H_N$) to provide a first index of arterial ageing,
(iv) determining a ratio of a product of the amplitude of $H_1$ with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide a second index of a arterial ageing, and
(v) comparing the first and second indexes to normative values of an index of arterial ageing to determine effect and cardiovascular risk.

7. The method according to claim 6 wherein the ratio of the amplitude of the first harmonic ($H_1$) to the sum of the amplitudes of the second and subsequent harmonics ($H_2 \ldots H_N$) is determined to provide the first index by using a formula:

$$\frac{H_1}{\{H_2 + H_3 + H_4 \ldots H_N\}},$$

and wherein $H_N$ is a frequency of between 6 to 12 Hz.

8. A method of determining ageing effect and cardiovascular risk in a human patient comprising:
measuring an arterial pulse waveform of the patient when the patient's heart is beating regularly,
(ii) extracting frequency dependent components of the pulse waveform,
(iii) determining a ratio of a square of an amplitude of a first harmonic ($H_1$) to a square of any one or to a sum of squares of amplitudes of a selected plurality of a second and subsequent harmonics ($H_2 \ldots H_N$) to provide a first index of arterial ageing,
(iv) determining a ratio of a product of an amplitude of $H_1$ with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide a second index of arterial ageing, and (v) comparing the first and second indexes to normative values of an index of arterial ageing to determine ageing effect and cardiovascular risk.

9. The method according to claim 8 wherein the ratio of the square of the amplitude of the first harmonic ($H_1$) to the sum of the squares of the amplitudes of the selected plurality of the second and subsequent harmonics ($H_2 \ldots H_N$) is determined to provide the first index by using a formula:

$$\frac{H_1^2}{\{H_2^2 + H_3^2 + H_4^2 \ldots H_N^2\}}.$$

10. A method of determining ageing effect and cardiovascular risk in a human patient comprising:
(i) measuring an arterial pulse waveform of the patient when the patient's heart is beating regularly,
(ii) extracting frequency dependent components of the pulse waveform,
(iii) determining a ratio of a product of an amplitude of a first harmonic ($H_1$) with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide an index of arterial ageing, and
(iv) comparing the index to normative values of an index of arterial ageing to determine ageing effect and cardiovascular risk.

11. The method according to claim 10 wherein the ratio of the product of the amplitude of the first harmonic ($H_1$) with the cosine of the phase $\phi$ of $H_1$, to the sum of the products of the amplitudes of the selected plurality of the second and subsequent harmonics ($H_2 \ldots H_N$) with the cosine of the phase $\phi$ of each harmonic in the selected plural is determined to provide the index by using a formula:

$$\frac{H_1 \cos\phi_1}{\{H_2 \cos\phi_2 + H_3 \cos\phi_3 + \ldots\}}.$$

12. A method of determining ageing effect and cardiovascular risk in a human patient comprising:
(i) measuring an arterial pulse waveform of the patient when the patient's heart is beating regularly,
(ii) extracting frequency dependent components of the pulse waveform,
(iii) determining a ratio of a sum of amplitudes of first and second harmonics to a sum of amplitudes of a selected plurality of third and subsequent harmonics ($H_3 \ldots H_N$) to provide a first index of arterial ageing by using a formula:

$$\frac{H_1 + H_2}{\{H_3 + H_4 \ldots H_N\}}.$$

(iv) determining a ratio of a product of an amplitude of $H_1$ with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide a second index of arterial ageinig, and (v) comparing the first and indexes to normative values of an index of arterial ageing to determine ageing effect and cardiovascular risk.

13. A method of determining ageing effect and cardiovascular risk in a human patient comprising:
(i) measuring an arterial pulse waveform of the patient when the patient's heart is beating regularly,
(ii) extracting frequency dependent components of the pulse waveform,
(iii) determining a ratio of a sum of squares of amplitudes of first and second harmonics to a sum of squares of amplitudes of a selected plurality of third and subsequent harmonics ($H_3 \ldots H_N$) to provide a first index of arterial ageing by using a formula:

$$\frac{H_1^2 + H_2^2}{\{H_3^2 + H_4^2 \ldots H_N^2\}}.$$

(iv) determining a ratio of a product of an amplitude of $H_1$ with a cosine of a phase $\phi$ of $H_1$ to a product of an amplitude of any one or to a sum of products of amplitudes of a selected plurality of a second and subsequent harmonics ($H_2 \ldots H_N$) with a cosine of a phase $\phi$ of each harmonic in the selected plurality to provide a second index of arterial ageing, and
(v) comparing the first and second indexes to normative values of an index of arterial ageing to determine ageing effect and cardiovascular risk.

14. The method according to claim 1 wherein the amplitude based values of the harmonics are measured by tonometric pressure, phase locked echo tracking diameter, Doppler flow or finger plethysmogram.

15. The method according to claim 1 wherein the arterial pulse waveform is measured from the patient's upper body.

16. The method according to claim 1 wherein the first index is used to assess the patient's response or potential response to drug therapy.

17. The method according to claim 1 wherein the amplitude based value of a harmonic number is replaced by a corresponding frequency band.

18. A method of determining ageing effect and cardiovascular risk in a human patient comprising:
(i) measuring an arterial pulse waveform of the patient when the patient's heart is beating regularly,
(ii) extracting frequency dependent components of the pulse waveform,
(iii) determining a ratio of a sum of products of an amplitude of each of a first and second harmonics with a cosine of a phase $\phi$ of the first and second harmonics respectively to a sum of products of an amplitude of each of a selected plurality of a third and subsequent harmonics ($H_3 \ldots H_N$) with a cosine of a phase $\phi$ of the respective third and subsequent harmonics to provide an index of arterial ageing by using a formula:

$$\frac{H_1\cos\phi_1 + H_2\cos\phi_2}{\{H_3\cos\phi_3 + H_4\cos\phi_4 \ldots \}}, \text{ and}$$

(iv) comparing the index to normative values of an index of arterial ageing to determine ageing effect and cardiovascular risk.

* * * * *

UNITED STATES PATENT AND TRADEMARK OFFICE
CERTIFICATE OF CORRECTION

PATENT NO. : 8,435,184 B2
APPLICATION NO. : 12/525014
DATED : May 7, 2013
INVENTOR(S) : O'Rourke et al.

It is certified that error appears in the above-identified patent and that said Letters Patent is hereby corrected as shown below:

In the Claims:

Column 11, Line 35, please replace "a arterial" with --arterial--.

Column 11, Line 52, please replace "measuring" with --(i) measuring--.

Column 12, Line 34, please replace "$H_1$," with --$H_1$--.

Column 12, Line 37, please replace "plural" with --plurality--.

Column 12, Lines 56-59, please replace the "." at the end of the formula with a --,--.

Column 13, Line 1, please replace "and indexes" with --and second indexes--.

Column 13, Lines 16-19, please replace the "." at the end of the formula with a --,--.

Signed and Sealed this
Twenty-fifth Day of June, 2013

Teresa Stanek Rea
*Acting Director of the United States Patent and Trademark Office*